United States Patent [19]

Sasaki et al.

[11] Patent Number: 5,688,875
[45] Date of Patent: Nov. 18, 1997

[54] HYDROPHILIC TETRAMETHYLXYLYLENECARBODIIMIDE

[75] Inventors: Eiji Sasaki; Yasuo Imashiro; Ikuo Takahashi; Naofumi Horie, all of Tokyo, Japan

[73] Assignee: Nisshinbo Industries, Inc., Tokyo, Japan

[21] Appl. No.: 455,413

[22] Filed: May 31, 1995

[30] Foreign Application Priority Data

Jun. 10, 1994 [JP] Japan ................... 6-152632

[51] Int. Cl.$^6$ .................................................. C08G 18/02
[52] U.S. Cl. .................. 525/452; 528/44; 525/453; 525/460; 252/182.2; 252/182.22; 564/252; 564/56; 560/25
[58] Field of Search ............... 528/44; 525/452, 525/453, 460; 252/182.2, 182.22; 564/252, 56; 560/25

[56] References Cited

U.S. PATENT DOCUMENTS

| | | | |
|---|---|---|---|
| 5,108,653 | 4/1992 | Taylor | 252/312 |
| 5,373,080 | 12/1994 | Imashiro et al. | 528/67 |
| 5,504,241 | 4/1996 | Pohl et al. | 560/25 |

*Primary Examiner*—Rachel Gorr
*Attorney, Agent, or Firm*—Kubovcik & Kubovcik

[57] ABSTRACT

A hydrophilic tetramethylxylylenecarbodiimide represented by the following formula (1):

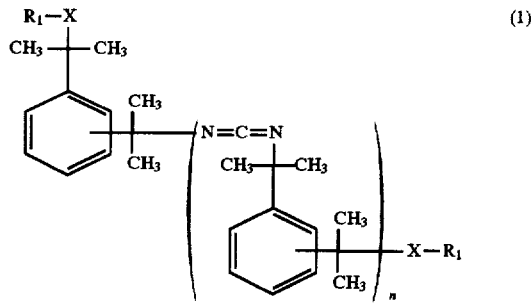

wherein n is an average polymerization degree and is an integer of 1 to 30; $R_1$ is a residue of an organic compound having a hydrophilic segment and at least one functional group reactive with an isocyanate group; and X is a group formed by the reaction of the functional group with the isocyanate group. The carbodiimide is free from the problems of the prior art, has good storage stability and accordingly is usable as an easy-to-handle crosslinking agent for hydrophilic resin.

4 Claims, No Drawings

HYDROPHILIC TETRAMETHYLXYLYLENECARBODIIMIDE

BACKGROUND OF THE INVENTION

1. Field of the Invention

The present invention relates to a novel hydrophilic carbodiimide. More particularly, the present invention relates to a hydrophilic carbodiimide having good storage stability owing to the reduced reactivity and accordingly usable as an easy-to-handle crosslinking agent for hydrophilic resin.

2. Description of the Prior Art

Carbodiimides, particularly polycarbodiimides, are known as a thermosetting resin having high heat resistance and find applications in molded materials, etc. obtained, for example, by hot-pressing a powdery polycarbodiimide.

Of the polycarbodiimides, aromatic polycarbodiimides have hitherto been used mainly. Recently, however, production and application of aliphatic polycarbodiimides were reported. For example, Japanese Patent Application Kokai (Laid-Open) No. 187029/1984 and Japanese Patent Publication No. 27450/1993 disclose a polycarbodiimide derived from isophorone diisocyanate and a method for crosslinking a resin for aqueous coating with said polycarbodiimide.

The above crosslinking of resin for aqueous coating utilizes a reaction between the carbodiimide group of polycarbodiimide and the active hydrogen of active-hydrogen compound. The reaction includes, for example, one between carbodiimide group and a carboxylic acid residue present in hydrophilic acrylic resin.

Conventional aliphatic polycarbodiimides (e.g. a polycarbodiimide derived from isophorone diisocyanate), however, are highly reactive. Therefore, they give rise to a reaction even after their addition to a resin for aqueous coating, providing a coating of poor storage stability and short shelf life.

Further, conventional aliphatic polycarbodiimides, when added to a resin for aqueous coating, etc., must be emulsified beforehand together with a surfactant, mechanically by the use of an expensive high-shear mixer, making complicated the emulsification operation. Moreover, conventional aliphatic polycarbodiimides, when emulsified, inevitably generate urea owing to the reaction with water, making short the storage stability of the emulsion.

OBJECT AND SUMMARY OF THE INVENTION

The present invention aims at providing a hydrophilic carbodiimide which is free from the problems of the prior art and which has good storage stability and accordingly is usable as an easy-to-handle crosslinking agent for hydrophilic resin.

According to the present invention there is provided a hydrophilic tetramethylxylylenecarbodiimide represented by the following general formula (1):

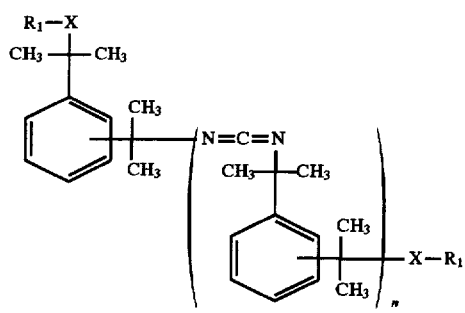

(wherein n is an average polymerization degree and is an integer of 1 to 30; $R_1$ is a residue of an organic compound having a hydrophilic segment and at least one functional group reactive with an isocyanate group; and X is a group formed by the reaction of said functional group with said isocyanate group).

DETAILED DESCRIPTION OF THE INVENTION

The present invention is hereinafter described in detail.

The hydrophilic carbodiimide of the present invention is represented by the above general formula (1) and is synthesized from (a) an isocyanate-terminated tetramethylxylylenecarbodiimide obtained from, for example, m-tetramethylxylylene diisocyanate

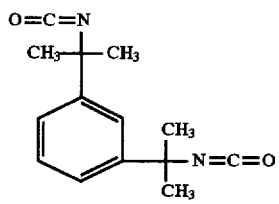

or p-tetramethylxylylene diisocyanate

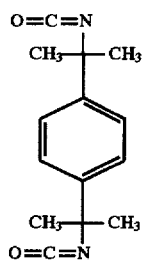

and (b) an organic compound having a hydrophilic segment and at least one functional group reactive with an isocyanate group (said organic compound is hereinafter abbreviated as hydrophilic segment compound).

In the above general formula (1), n is an integer of 1—30 and is an average polymerization degree of the hydrophilic carbodiimide of the present invention. As easily appreciated from the formula, the present carbodiimide has stereoisomers.

The present hydrophilic carbodiimide can be produced specifically by subjecting tetramethylxylylene diisocyanate to a condensation reaction (carbon dioxide removal takes place in the reaction) to synthesize an isocyanate-terminated tetramethylxylylenecarbodiimide and then reacting it with a hydrophilic segment compound.

The above production of isocyanate-terminated tetramethylxylylenecarbodiimide can be conducted basically by conventional processes for production of polycarbodiimide [U.S. Pat. No. 2,941,956; Japanese Patent Publication No. 33279/1972; J. Org. Chem., 28, 2069–2076 (1963); Chemical Review 1981, Vol. 81, No. 4, pp. 619–621].

The above condensation reaction of tetramethylxylylene diisocyanate wherein carbon dioxide removal takes place, proceeds in the presence of a carbodiimidization catalyst. The catalyst includes, for example, 1-phenyl-2-phospholene-1-oxide, 3-methyl-2-phospholene-1-oxide, 1-ethyl-2-phospholene-1-oxide, 1-ethyl-3-methyl-2-phospholene-1-oxide, 3-methyl-1-phenyl-2-phospholene-1-oxide and 3-phospholene isomers thereof. Of these, 3-methyl-1-phenyl-2-phospholene-1-oxide is preferred in view of the reactivity.

The temperature of the above condensation reaction is preferably about 80°–180° C. When the temperature is lower than 80° C., the reaction time is very long. When the temperature is higher than 180° C., side reactions take place, making it difficult to obtain a carbodiimide of good quality.

The condensation degree obtained is preferably 30 or less. A condensation degree higher than 30 results in lower water dispersibility. In order to complete the condensation reaction quickly, the reaction of tetramethylxylylene diisocyanate is conducted in a stream of an inert gas such as nitrogen or the like.

As the hydrophilic segment compound, there can be used various compounds. They include, for example, a dialkylamino-alcohol represented by the following general formula:

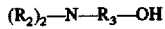

(wherein $R_2$ is a lower alkyl group of, for example, 1–4 carbon atoms; and $R_3$ is an alkylene or oxyalkylene of, for example, 1–10 carbon atoms). Specific examples of the dialkylamino-alcohol are 2-dimethylaminoethanol, 2-diethylaminoethanol, 3-methylamino-1-propanol, 3-diethylamino-1-propanol, 1-diethyl-amino-2-propanol, 5-diethylamino-2-propanol and 2-(di-n-butyl-amino) ethanol. 2-Dimethylaminoethanol is particularly preferred.

The reaction product between isocyanate-terminated tetramethylxylylenecarbodiimide and dialkylaminoalcohol is quaternized with a known quaternizing agent such as dimethyl sulfate, methyl p-toluenesulfonate or the like, whereby an intended hydrophilic tetramethylxylylenecarbodiimide can be obtained.

When the dialkylaminoalcohol is used as the hydrophilic segment compound, the resulting hydrophilic tetramethylxylylene-carbodiimide of the present invention has the following molecular structure and is a cationic type. In the following formula, R' is a group derived from the quaternizing agent used.

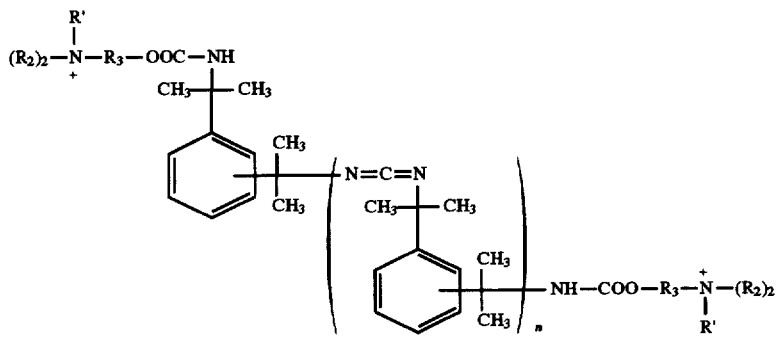

The hydrophilic segment compound also includes a salt of an alkylsulfonic acid having at least one reactive hydroxyl group, said salt being represented by the following general formula:

(wherein $R_4$ is an alkylene of 1–10 carbon atoms; and $R_5$ is an alkali metal). Specific examples of the alkylsulfonic acid salt are sodium hydroxyethanesulfonate and sodium hydroxypropane-sulfonate. Sodium hydroxypropane-sulfonate is preferred particularly.

When the salt of an alkylsulfonic acid having at least one reactive hydroxyl group is used as the hydrophilic segment compound, the resulting hydrophilic tetramethylxylylenecarbodiimide of the present invention has the following molecular structure and is an anionic type.

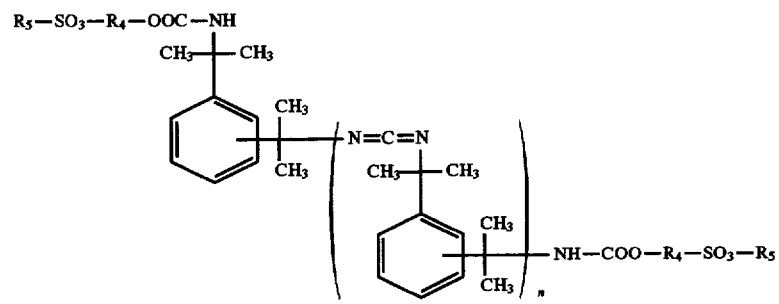

The hydrophilic segment compound also includes a poly(alkylene oxide) having at least one reactive hydroxyl group, blocked with an alkoxyl group at one end, said poly(alkylene oxide) being represented by the following general formula:

$$R_6-O-(CH_2-CHR_7-O-)_mH$$

(wherein m is an integer of 4–30; $R_6$ is a lower alkyl group of, for example, 1–4 carbon atoms; and $R_7$ is a hydrogen atom or a methyl group). Specific examples of the poly(alkylene oxide) are poly(ethylene oxide) monomethyl ether, poly(ethylene oxide) monoethyl ether, poly(ethylene oxide-propylene oxide) monomethyl ether and poly(ethylene oxide-propylene oxide) monoethyl ether. Poly(ethylene oxide) monomethyl ether is preferred particularly.

When the poly(alkylene oxide) having at least one reactive hydroxyl group, blocked with an alkoxyl group at one end is used as the hydrophilic segment compound, the resulting hydrophilic tetramethylxylylenecarbodiimide of the present invention has the following molecular structure and is a nonionic type.

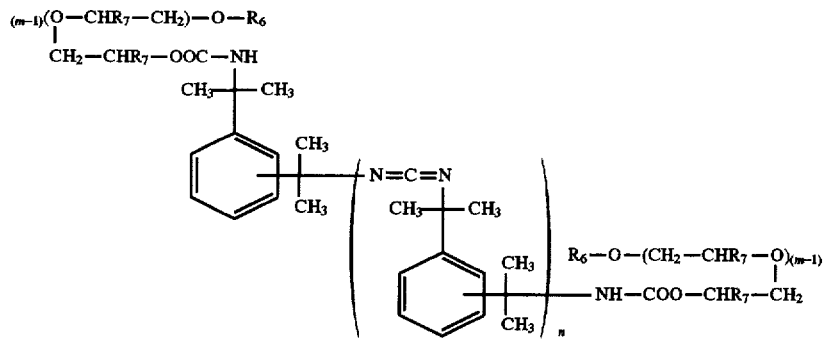

The hydrophilic segment compound also includes a dialkylaminoalkylamine represented by the following general formula:

$$(R_8)_2-N-R_9-NH_2$$

(wherein $R_8$ is a lower alkyl group of, for example, 1–4 carbon atoms; and $R_9$ is an alkylene or oxyalkylene of, for example, 1–10 carbon atoms). Specific examples of the dialkylaminoalkylamine are 3-dimethylamino-n-propylamine, 3-diethylamino-n-propylamine and 2-diethylamino-ethylamine. 3-Dimethylamino-n-propylamine is preferred particularly.

The reaction product between isocyanate-terminated tetramethylxylylenecarbodiimide and dialkylaminoalkylamine is quaternized with a known quaternizing agent such as dimethyl sulfate, methyl p-toluenesulfonate or the like, whereby an intended hydrophilic tetramethylxylylenecarbodiimide can be obtained.

When the dialkylaminoalkylamine is used as the hydrophilic segment compound, the resulting hydrophilic tetramethylxylylenecarbodiimide of the present invention has the following molecular structure and is a cationic type. In the following formula, R" is a group derived from the quaternizing agent.

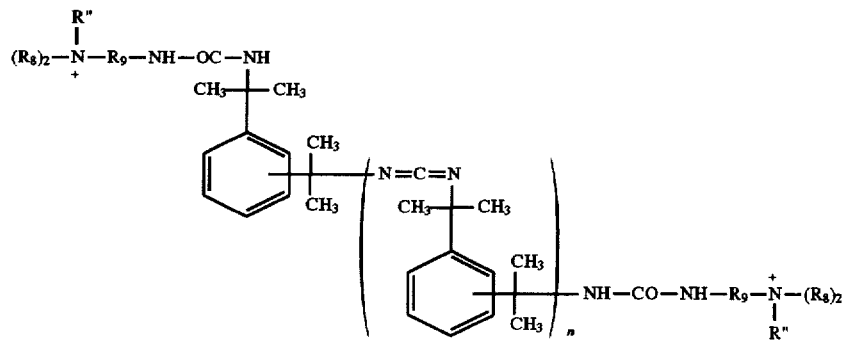

The above addition reaction between isocyante terminated tetramethylxylylenecarbodiimide and hydrophilic segment compound may use a catalyst but proceeds easily only by heating. The reaction temperature can be about 60°–40° C., preferably about 80°–120° C. When the reaction temperature is lower than about 60° C., the reaction time is very long. When the reaction temperature is higher than about 140° C., side reactions take place, making it impossible to obtain a hydrophilic carbodiimide of good quality.

The quaternization reaction of the addition product between isocyanate-terminated tetramethylxylylenecarbodiimide and hydrophilic segment compound (dialkylaminoalcohol or dialkylaminoalkylamine), with the quaternizing agent can be conducted by reacting said addition product with an equivalent amount of a quaternizing agent.

The hydrophilic tetramethylxylylenecarbodiimide produced as above can be used in various forms. When it is added to an aqueous coating, etc., it may be added as it is, but it is preferably added in the form of an aqueous solution or dispersion in view of easier mixing. In the present invention, the term "hydrophilic" used for tetramethylxylylenecarbodiimide refers to that the tetramethylxylylenecarbodiimide is water-soluble or self-emulsifiable in water and is uniformly compatible with water.

Appropriate selection of the hydrophilic segment compound allows for production of any of three kinds (cationic type, anionic type and nonionic type) of hydrophilic tetramethylxylylenecarbodiimides. Therefore, it is possible to provide any hydrophilic carbodiimide suited for the ionicity of a hydrophilic resin to which said carbodiimide is to be added.

The present invention is hereinafter described in more detail with reference to Examples.

(Synthesis of hydrophilic tetramethylxylylenecarbodiimides)

EXAMPLE 1

700 g of m-tetramethylxylylene diisocyanate was reacted with 14 g of a carbodiimidization catalyst (3-methyl-1-phenyl-2-phospholene-1-oxide) at 180° C. for 18 hours to obtain an isocyanate-terminated tetramethylxylylenecarbodiimide (polymerization degree=4). 50.2 g of the carbodiimide was reacted with 8.9 g. of 2-dimethylaminoethanol at 80° C. for 24 hours. Thereto was added 18.6 g of methyl p-toluenesulfonate, followed by stirring for 1 hour to conduct quaternization. Thereto was slowly added 77.7 g of distilled water so as to give a resin concentration of 50% by weight, to obtain a yellow transparent carbodiimide solution. The solution, when stored in a constant-temperature chamber of 25° C. for 12 months, showed neither separation nor precipitation and was very stable.

EXAMPLE 2

700 g of m-tetramethylxylylene diisocyanate was reacted with 14 g of a carbodiimidization catalyst (3-methyl-1-phenyl-2-phospholene-1-oxide) at 180° C. for 18 hours to obtain an isocyanate-terminated tetramethylxylylenecarbodiimide (polymerization degree=4). 50.2 g of the carbodiimide was reacted with 10.2 g of 3-dimethylamino-n-propylamine at 80° C. for 1 hour. Thereto was added 18.6 g of methyl-p-toluenesulfonate, followed by stirring for 1 hour to conduct quaternization. Thereto was slowly added 79 g of distilled water so as to give a resin concentration of 50% by weight, to obtain a yellow transparent carbodiimide solution. The solution, when stored in a constant-temperature chamber of 25° C. for 12 months, showed neither separation nor precipitation and was very stable.

EXAMPLE 3

700 g of m-tetramethylxylylene diisocyanate was reacted with 14 g of a carbodiimidization catalyst (3-methyl-1-phenyl-2-phospholene-1-oxide) at 180° C. for 32 hours to obtain an isocyanate-terminated tetramethylxylylenecarbodiimide (polymerization degree=10). 52.7 g of the carbodiimide was reacted with 5.1 g of 3-dimethylamino-n-propylamine at 80° C. for 1 hour. Thereto was added 9.3 g of methyl p-toluenesulfonate, followed by stirring for 1 hour to conduct quaternization. Thereto was slowly added 67.1 g of distilled water so as to give a resin concentration of 50% by weight, to obtain an emulsion-like carbodiimide solution. The solution, when stored in a constant-temperature chamber of 25° C. for 12 months, showed neither separation nor precipitation and was very stable.

EXAMPLE 4

700 g of m-tetramethylxylylene diisocyanate was reacted with 14 g of a carbodiimidization catalyst (3-methyl-1-phenyl-2-phospholene-1-oxide) at 180° C. for 18 hours to obtain an isocyanate-terminated tetramethylxylylenecarbodiimide (polymerization degree=4). 210.5 g of the carbodiimide was reacted with 40.9 g of 3-dimethylamino-n-propylamine at 80° C. for 1 hour. Thereto was added 50.5 g of dimethyl sulfate, followed by stirring for 1 hour to conduct quaternization. Thereto was slowly added 301.9 g of distilled water so as to give a resin concentration of 50% by weight, to obtain a yellow transparent carbodiimide solution. The solution, when stored in a constant-temperature chamber of 25° C. for 12 months, showed neither separation nor precipitation and was very stable.

EXAMPLE 5

700 g of m-tetramethylxylylene diisocyanate was reacted with 14 g of a carbodiimidization catalyst (3-methyl-1-phenyl-2-phospholene-1-oxide) at 180° C. for 32 hours to obtain an isocyanate-terminated tetramethylxylylenecarbodiimide (polymerization degree=10). 105.3 g of the carbodiimide was reacted with 10.2 g of 3-dimethylamino-n-propylamine at 80° C. for 1 hour. Thereto was added 12.6 g of dimethyl sulfate, followed by stirring for 1 hour to conduct quaternization. Thereto was slowly added 128.1 g of distilled water so as to give a resin concentration of 50% by weight, to obtain an emulsion-like carbodiimide solution. The solution, when stored in a constant-temperature chamber of 25° C. for 12 months, showed neither separation nor precipitation and was very stable.

EXAMPLE 6

700 g of m-tetramethylxylylene diisocyanate was reacted with 14 g of a carbodiimidization catalyst (3-methyl-1-phenyl-2-phospholene-1-oxide) at 180° C. for 32 hours to obtain an isocyanate-terminated tetramethylxylylenecarbodiimide (polymerization degree=10). 224.4 g of the carbodiimide was reacted with 41.2 g of sodium hydroxypropanesulfonate at 100° C. for 24 hours. Thereto was slowly added, at 80° C., 619.7 g of distilled water so as to give a resin concentration of 30% by weight, to obtain an emulsion-like carbodiimide solution. The solution, when stored in a constant-temperature chamber of 25° C. for 12 months, showed neither separation nor precipitation and was very stable.

EXAMPLE 7

700 g of m-tetramethylxylylene diisocyanate was reacted with 14 g of a carbodiimidization catalyst (3-methyl-1-phenyl-2-phospholene-1-oxide) at 180° C. for 22 hours to obtain an isocyanate-terminated tetramethylxylylenecarbodiimide (polymerization degree=5). 124.4 g of the carbodiimide was reacted with 63.6 g of poly(oxyethylene) monomethyl ether having a polymerization degree (m) of about 6 at 100° C. for 48 hours. Thereto was slowly added, at 50° C., 282.0 g of distilled water so as to give a resin concentration of 40% by weight, to obtain a yellow transparent carbodiimide solution. The solution, when stored in a constant-temperature chamber of 25° C. for 12 months, showed neither separation nor precipitation and was very stable.

EXAMPLE 8

700 g of m-tetramethylxylylene diisocyanate was reacted with 14 g of a carbodiimidization catalyst (3-methyl-1-phenyl-2-phospholene-1-oxide) at 180° C. for 22 hours to obtain an isocyanate-terminated tetramethylxylylenecarbodiimide (polymerization degree=5). 124.4 g of the carbodiimide was reacted with 115.0 g of poly(oxyethylene) monomethyl ether having a polymerization degree (m) of about 12 at 100° C. for 48 hours. Thereto was slowly added, at 50° C. 359.1 g of distilled water so as to give a resin concentration of 40% by weight, to obtain a yellow transparent carbodiimide solution. The solution, when stored in a constant temperature chamber of 25° C. for 12 months, showed neither separation nor precipitation and was very stable.

EXAMPLE 9

700 g of m-tetramethylxylylene diisocyanate was reacted with 14 g of a carbodiimidization catalyst (3-methyl-1-phenyl-2-phospholene-1-oxide) at 180° C. for 32 hours to obtain an isocyanate-terminated tetramethylxylylenecarbodiimide (polymerization degree=10). 224.4 g of the carbodiimide was reacted with 63.6 g of poly(oxyethylene) monomethyl ether having a polymerization degree (m) of about 6 at 100° C. for 48 hours. Thereto was slowly added, at 50° C., 432 g of distilled water so as to give a resin concentration of 40% by weight, to obtain an emulsion-like carbodiimide solution. The solution, when stored in a constant-temperature chamber of 25° C. for 12 months, showed neither separation nor precipitation and was very stable.

EXAMPLE 10

700 g of m-tetramethylxylylene diisocyanate was reacted with 14 g of a carbodiimidization catalyst (3-methyl-1-phenyl-2-phospholene-1-oxide) at 180° C. for 32 hours to obtain an isocyanate-terminated tetramethylxylylenecarbodiimide (polymerization degree=10). 224.4 g of the carbodiimide was reacted with 82.6 g of poly(oxyethylene) monomethylether having a polymerization degree (m) of about 8 at 100° C. for 48 hours. Thereto was slowly added, at 50° C., 716.3 g of distilled water so as to give a resin concentration of 30% by weight, to obtain an emulsion-like carbodiimide solution. The solution, when stored in a constant-temperature chamber of 25° C. for 12 months, showed neither separation nor precipitation and was very stable.

EXAMPLE 11

700 g of m-tetramethylxylylene diisocyanate was reacted with 14 g of a carbodiimidization catalyst (3-methyl-1-phenyl-2-phospholene-1-oxide) at 180° C. for 32 hours to obtain an isocyanate-terminated tetramethylxylylenecarbodiimide (polymerization degree=10). 224.4 g of the carbodiimide was reacted with 115.0 g of poly(oxyethylene) monomethyl ether having a polymerization degree (m) of about 12 at 100° C. for 48 hours. Thereto was slowly added, at 50° C., 509.1 g of distilled water so as to give a resin concentration of 40% by weight, to obtain a yellow transparent carbodiimide solution. The solution, when stored in a constant-temperature chamber of 25° C. for 12 months, showed neither separation nor precipitation and was very stable.

EXAMPLE 12

700 g of m-tetramethylxylylene diisocyanate was reacted with 14 g of a carbodiimidization catalyst (3-methyl-1-phenyl-2-phospholene-1-oxide) at 180° C. for 58 hours to obtain an isocyanate-terminated tetramethylxylylenecarbodiimide (polymerization degree=15). 324.4 g of the carbodiimide was reacted with 115.0 g of poly(oxyethylene) monomethyl ether having a polymerization degree (m) of about 12 at 100° C. for 48 hours. Thereto was slowly added, at 50° C., 659.1 g of distilled water so as to give a resin concentration of 40% by weight, to obtain an emulsion-like carbodiimide solution. The solution, when stored in a constant-temperature chamber of 25° C. for 12 months, showed neither separation nor precipitation and was very stable.

EXAMPLE 13

700 g of m-tetramethylxylylene diisocyanate was reacted with 14 g of a carbodiimidization catalyst (3-methyl-1-phenyl-2-phospholene-1-oxide) at 180° C. for 58 hours to obtain an isocyanate-terminated tetramethylxylylenecarbodiimide (polymerization degree=15). 324.4 g of the carbodiimide was reacted with 160.2 g of poly(oxyethylene) monomethyl ether having a polymerization degree (m) of about 18 at 100° C. for 48 hours. Thereto was slowly added, at 50° C., 726.9 g of distilled water so as to give a resin concentration of 40% by weight, to obtain a yellow transparent carbodiimide solution. The solution, when stored in a constant-temperature chamber of 25° C. for 12 months, showed neither separation nor precipitation and was very stable.

Comparative Example 1

700 g of isophorone diisocyanate was reacted with 14 g of a carbodiimidization catalyst (3-methyl-1-phenyl-2-phospholene-1-oxide) at 180° C. for 6 hours to obtain an isocyanate-terminated isophoronecarbodiimide (polymerization degree=4). 93.4 g of the carbodiimide was reacted with 17.8 g of 2-dimethylaminoethanol at 80° C. for 24 hours. Thereto was added 37.2 g of methyl p-toluenesulfonate, followed by stirring for 1 hour to conduct quaternization. Thereto was slowly added 148.4 g of distilled water so as to give a resin concentration of 50% by weight, to obtain a yellow transparent carbodiimide solution. The solution, when stored in a constant-temperature chamber of 25° C., became cloudy and showed separation in 3 months.

Comparative Example 2

700 g of isophorone diisocyanate was reacted with 14 g of a carbodiimidization catalyst (3-methyl-1-phenyl-2-phospholene-1-oxide) at 180° C. for 6 hours to obtain an isocyanate-terminated isophoronecarbodiimide (polymerization degree=4). 93.4 g of the carbodiimide was reacted with 20.4 g of 3-dimethylamine-n-propylamine at 80° C. for 1 hour. Thereto was added 37.2 g of methyl p-toluenesulfonate, followed by stirring for 1 hour to conduct quaternization. Thereto was slowly added 151 g of distilled water so as to give a resin concentration of 50% by weight, to obtain a yellow transparent carbodiimide solution. The solution, when stored in a constant-temperature chamber of 25° C., became cloudy and showed separation in 3 months.

Comparative Example 3

700 g of isophorone diisocyanate was reacted with 14 g of a carbodiimidization catalyst (3-methyl-1-phenyl-2-phospholene-1-oxide) at 180° C. for 14 hours to obtain an isocyanate-terminated isophoronecarbodiimide (polymerization degree=10). 200.2 g of the carbodiimide was reacted with 20.4 g of 3-dimethylamine-n-propylamine at 80° C. for 1 hour. Thereto was added 37.2 g of methyl p-toluenesulfonate, followed by stirring for 1 hour to conduct quaternization. Thereto was slowly added 257.8 g of distilled water so as to give a resin concentration of 50% by weight, to obtain an emulsion-like carbodiimide solution. The solution, when stored in a constant-temperature chamber of 25° C., showed separation in 2 months.

Comparative Example 4

700 g of isophorone diisocyanate was reacted with 14 g of a carbodiimidization catalyst (3-methyl-1-phenyl-2-phospholene-1-oxide) at 180° C. for 14 hours to obtain an isocyanate-terminated isophoronecarbodiimide (polymerization degree=10). 200.2 g of the carbodiimide was reacted with 41.2 g of sodium hydroxypropanesulfonate at 100° C. for 24 hours. Thereto was slowly added, at 80° C., 563.3 g of distilled water so as to give a resin concentration of 30% by weight, to obtain an emulsion-like carbodiimide solution. The solution, when stored in a constant-temperature chamber of 25° C., showed separation in 2 months.

Comparative Example 5

700 g of isophorone diisocyanate was reacted with 14 g of a carbodiimidization catalyst (3-methyl-1-phenyl-2-phospholene-1-oxide) at 180° C. for 8 hours to obtain an isocyanate-terminated isophoronecarbodiimide (polymerization degree=5). 111.2 g of the carbodiimide was reacted with 63.6 g of poly(oxyethylene) monomethyl ether having a polymerization degree (m) of about 6 at 100° C. for 24 hours. Thereto was slowly added, at 50° C., 262.2 g of distilled water so as to give a resin concentration of 40% by weight, to obtain a yellow transparent carbodiimide solution. The solution, when stored in a constant-temperature chamber of 25° C., became cloudy and showed separation in 4 months.

Comparative Example 6

700 g of isophorone diisocyanate was reacted with 14 g of a carbodiimidization catalyst (3-methyl-1-phenyl-2-phospholene-1-oxide) at 180° C. for 14 hours to obtain an isocyanate-terminated isophoronecarbodiimide (polymerization degree=10). 200.2 g of the carbodiimide was reacted with 82.6 g of poly(oxyethylene) monomethyl ether having a polymerization degree (m) of about 8 at 100° C. for 48 hours. Thereto was slowly added, at 50° C., 660 g of distilled water so as to give a resin concentration of 30% by weight, to obtain an emulsion-like carbodiimide solution. The solution, when stored in a constant-temperature chamber of 25° C., showed separation in 2 months.

Comparative Example 7

700 g of isophorone diisocyanate was reacted with 14 g of a carbodiimidization catalyst (3-methyl-1-phenyl-2-phospholene-1-oxide) at 180° C. for 14 hours to obtain an isocyanate-terminated isophoronecarbodiimide (polymerization degree=10). 200.2 g of the carbodiimide was reacted with 115.0 g of poly(oxyethylene) monomethyl ether having a polymerization degree (m) of about 12 at 100° C. for 24 hours. Thereto was slowly added, at 50° C., 472.8 g of distilled water so as to give a resin concentration of 40% by weight, to obtain a yellow transparent carbodiimide solution. The solution, when stored in a constant-temperature chamber of 25° C., became cloudy and showed separation in 4 months.

The results of syntheses in Examples 1–13 and Comparative Examples 1–7 are shown in Tables 1–1 and 1–2. As is clear from Tables 1–1 and 1–2, the hydrophilic tetramethylxylylenecarbodiimides of Examples 1–13 according to the present invention are superior in storage stability to the hydrophilic isophoronecarbodiimides of Comparative Examples 1–7.

TABLE 1-1

| | Number of carbodi-imide | Hydrophilic segment compound | Ionicity | Appearance of aqueous solution | Concentration of aqueous solution | stability |
|---|---|---|---|---|---|---|
| Example 1 | 4 | Quaternary salt of 2-dimethyl-aminoethanol | Cationic | Transparent | 50% | No change after 12 months |
| 2 | 4 | Quaternary salt of 3-di-methylamino-n-propyl-amine | Cationic | Transparent | 50% | Same as above |
| 3 | 10 | Same as above | Cationic | Emulsion-like | 50% | Same as above |
| 4 | 4 | Same as above | Cationic | Transparent | 50% | Same as above |
| 5 | 10 | Same as above | Cationic | Emulsion-like | 50% | Same as above |
| 6 | 10 | Sodium hydroxy-propanesulfonate | Anionic | Emulsion-like | 30% | Same as above |
| 7 | 5 | Polyoxyethylene monomethyl ether (m = about 6) | Nonionic | Transparent | 40% | Same as above |
| 8 | 5 | Polyoxyethylene monomethyl ether (m = about 12) | Nonionic | Transparent | 40% | Same as above |
| 9 | 10 | Polyoxyethylene monomethyl ether (m = about 6) | Nonionic | Emulsion-like | 40% | Same as above |
| 10 | 10 | Polyoxethylene monomethyl ether (m = about 8) | Nonionic | Emulsion-like | 30% | Same as above |
| 11 | 10 | Polyoxyethylene monomethyl ether (m = about 12) | Nonionic | Transparent | 40% | Same as above |

TABLE 1-1-continued

| Number of carbodi-imide | Hydrophilic segment compound | Ionicity | Appearance of aqueous solution | Concentration of aqueous solution | stability |
|---|---|---|---|---|---|
| 12 | 15 | Same as above | Nonionic | Emulsion-like | 40% | Same as above |
| 13 | 15 | Polyoxyethylene monomethyl ether (m = about 18) | Nonionic | Transparent | 40% | Same as above |

TABLE 1-2

| | Number of carbodi-imide | Hydrophilic segment compound | Ionicity | Appearance of aqueous solution | Concentration of aqueous solution | stability |
|---|---|---|---|---|---|---|
| Comparative Example 1 | 4 | Quaternary salt of 2-dimethyl-aminoethanol | Cationic | Transparent | 50% | Became cloudy and showed separation in 3 months |
| 2 | 4 | Quaternary salt of 3-di-methylamino-n-propylamine | Cationic | Transparent | 50% | Same as above |
| 3 | 10 | Same as above | Cationic | Emulsion-like | 50% | Showed separation in 2 months |
| 4 | 10 | Sodium hydroxypropane-sulfonate | Anionic | Emulsion-like | 30% | Same as above |
| 5 | 5 | polyoxyethylene monomethyl ether (m = about 6) | Nonionic | Transparent | 40% | Became cloudy and showed separation in 4 months |
| 6 | 10 | polyoxyethylene monomethyl ether (m = about 8) | Nonionic | Emulsion-like | 30% | Showed separation in 2 months |
| 7 | 10 | polyoxyethylene monomethyl ether (m = about 12) | Nonionic | Transparent | 40% | Became cloudy and showed separation in 4 months |

Reference Example (Reactions between hydrophilic tetramethylxylylenecarbodiimides and aqueous resins)

Each of the aqueous carbodiimide solutions obtained in Examples 7, 10, and 11 and Comparative Examples 5, 6 and 7 was added to a solution of a styrene-acrylic resin of acid value=300 (solvent in solution: water/alcohol=95/5, resin concentration in solution=30% by weight) so that the carbodiimide group and the carboxyl group became 1:1 in equivalent. Each of the resulting mixtures was measured for viscosity change at 25° C. Further, each mixture was coated on a polyethylene terephthalate film by the use of an applicator so that the resulting film had a thickness of 100 μm; the film was dried at 80° C. for 5 minutes; and the dried film was cut into a piece of 5 cm×5 cm and immersed in 300 ml of distilled water for 24 hours to observe the change of the film condition.

The results of the above test are shown in Table 2.

TABLE 2

| Kind of carbodiimide solution | Weight of carbodi-imide solution | Weight of styrene-acrylic resin | Mixture viscosity right af-ter mixing | Mixture viscosity after 3 days | Mixture viscosity after 1 week | Appearance of film before immersion in water | Appearance of film after 24 hours immersion in water |
|---|---|---|---|---|---|---|---|
| Example 7 | 45.7 g | 30 g | 181 cp | 215 cp | 325 cp | Transparent | Transparent (no Change) |
| 10 | 49.7 g | 30 g | 170 cp | 228 cp | 380 cp | Transparent | Transparent (no Change) |
| 11 | 41.2 g | 30 g | 195 cp | 235 cp | 392 cp | Transparent | Transparent (no Change) |
| Comparative Example 5 | 42.5 g | 30 g | 190 cp | 795 cp | gelling | Transparent | White |
| 6 | 45.8 g | 30 g | 178 cp | 850 cp | gelling | Transparent | White and partial peeling |
| 7 | 38.3 g | 30 g | 206 cp | 830 cp | gelling | Transparent | White |

As is clear from Table 2, the hydrophilic tetramethylxylylenecarbodimides of Examples 7, 10 and 11 according to the present invention are superior to the aqueous isophoronecarbodiimides of Comparative Examples 5, 6 and 7 in stability after addition to hydrophilic resin as well as in potency as crosslinking agent.

What is claimed is:

1. A hydrophilic tetramethylxylylenecarbodiimide represented by the formula:

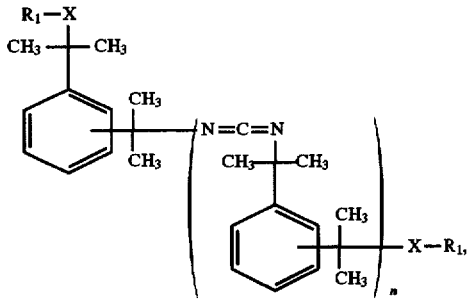

wherein n is an average polymerization degree and is an integer of 1 to 30; X is —OOC—HN—; and $R_1$ is a residue of a quaternary ammonium salt of a dialkylaminoalcohol represented by the formula:

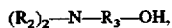

$(R_2)_2$—N—$R_3$—OH, wherein $R_2$ is lower alkyl and $R_3$ is alkylene or oxyalkylene of 1–10 carbon atoms.

2. A hydrophilic tetramethylxylylenecarbodiimide represented by the formula:

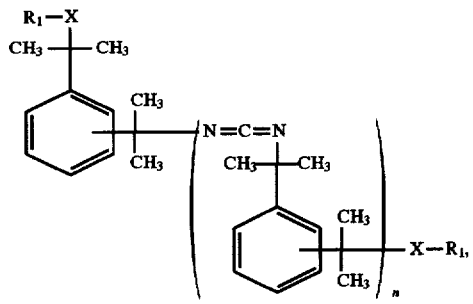

wherein n is an average polymerization degree and is an integer of 1 to 30; X is —OOC—HN—; and $R_1$ is a residue of a salt of an alkylsulfonic acid having at least one reactive hydroxyl group, said salt being represented by the formula:

$R_5$—$SO_3$—$R_4$—OH wherein $R_4$ is alkylene of 1–10 carbon atoms and $R_5$ is an alkali metal.

3. A hydrophilic tetramethylxylylenecarbodiimide represented by the formula:

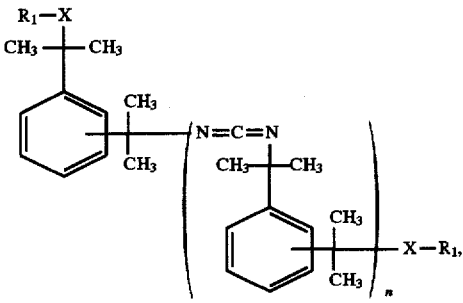

wherein n is an average polymerization degree and is an integer of 1 to 30; X is —NH—OC—NH—; and $R_1$ is a residue of an organic compound having a hydrophilic segment and at least one functional group reactive with an isocyanate group.

4. A hydrophilic tetramethylxylylenecarbodiimide according to claim 3, wherein $R_1$ is a residue of a quaternary ammonium salt of a dialkylaminoalkylamine represented by the following formula:

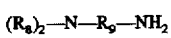

$(R_8)_2$—N—$R_9$—$NH_2$ wherein $R_8$ is a lower alkyl group; and $R_9$ is an alkylene or oxyalkylene having 1–10 carbon atoms.

* * * * *